United States Patent [19]
Van Iseghem et al.

[11] Patent Number: 5,334,485
[45] Date of Patent: Aug. 2, 1994

[54] ACID SOLUBLE PHOTO-RESIST COMPRISING A PHOTOSENSITIVE POLYMER

[75] Inventors: Lawrence C. Van Iseghem; Alexander S. Gybin, both of Duluth, Minn.

[73] Assignee: The Chromaline Corporation, Duluth, Minn.

[21] Appl. No.: 788,134

[22] Filed: Nov. 5, 1991

[51] Int. Cl.$^5$ .................... G03F 7/038; C08F 8/44; G03C 1/72
[52] U.S. Cl. .................... 430/287; 430/281; 522/151; 525/279; 525/327.1; 525/59; 526/259; 526/263; 526/265
[58] Field of Search ............ 430/270, 287, 281, 285, 430/283, 906, 286, 908, 910; 522/151; 526/259, 265; 525/279, 203, 327.1, 326.7, 59

[56] References Cited

U.S. PATENT DOCUMENTS

| | | | |
|---|---|---|---|
| 2,811,443 | 10/1957 | Robertson et al. | 96/35 |
| 2,811,510 | 10/1957 | Leubner et al. | 260/67.5 |
| 2,887,376 | 5/1959 | Tupis | 96/35 |
| 2,908,667 | 10/1959 | Williams | 260/79.3 |
| 3,873,500 | 3/1975 | Kato et al. | 260/47 UA |
| 3,882,084 | 5/1975 | Tato et al. | 260/47 UA |
| 3,936,429 | 2/1976 | Seoka et al. | 260/79.3 M |
| 4,272,620 | 6/1981 | Ichimura | 525/61 |
| 4,339,524 | 7/1982 | Ichimura et al. | 430/270 |
| 4,444,868 | 4/1984 | Ichimura | 430/285 |
| 4,478,977 | 10/1984 | Sperry et al. | 525/61 |
| 4,554,240 | 11/1985 | Schulz et al. | 430/285 |
| 4,564,580 | 1/1986 | Ichimura et al. | 430/281 |
| 4,581,318 | 4/1986 | Lee et al. | 430/270 |
| 4,764,449 | 8/1988 | Van Iseghem | 430/162 |
| 4,777,114 | 10/1988 | Ichimura et al. | 430/270 |
| 4,917,993 | 4/1990 | Mukunoki et al. | 430/523 |
| 4,920,030 | 4/1990 | Ichimura et al. | 430/270 |

FOREIGN PATENT DOCUMENTS

| | | |
|---|---|---|
| 901370 | 5/1972 | Canada . |
| 092901 | 11/1983 | European Pat. Off. . |
| 0130804-A2 | 6/1984 | European Pat. Off. . |
| 0290133 | 11/1988 | European Pat. Off. . |
| 313221 | 4/1989 | European Pat. Off. . |
| 883782 | 6/1961 | United Kingdom . |

OTHER PUBLICATIONS

Borden et al., "Photosensitive Polymers", *Chemical Abstracts*, vol. 72, p. 10 (1970).
Borden et al., "Light-sensitive Polymers", *Radiation Chemistry and Photochemistry*, vol. 72, p. 395 (1970) abstract only.
Borden et al., "Photopolymer Design: Photocrosslinkable Styrylpyridinium Substituted Vinyl Polymers with Absorption Maxima from 270 nm to 540 nm", *MakromolekulareChemi*, vol. 178, pp. 3035–3049 (1977).
Unruh et al., "Condensation of Poly(4-vinylacetophenone) with Various Araldehydes", *Journal of Applied Polymer Science*, vol. III, Issue No. 9, pp. 310–315 (1960).

(List continued on next page.)

*Primary Examiner*—Marion E. McCamish
*Assistant Examiner*—Rosemary Ashton
*Attorney, Agent, or Firm*—Merchant, Gould, Smith, Edell, Welter & Schmidt

[57] ABSTRACT

Photosensitive, photocurable, compositions contain a polymeric backbone which are basic in an aqueous environment having a pendant photosensitive group. The pendant groups are styryl-amine or nitrogen heterocyclic groups which contain an ethylenically unsaturated photocross-linking group. The pendant styryl-amine or nitrogen heterocyclic groups can cross-link two polymer chains by photo addition through ethylenically unsaturated groups in the styryl moiety forming a cyclobutane crosslinked site. The cross-linking is accomplished by irradiating the material with visible light or ultraviolet radiation of appropriate wave length, depending on the absorbitivity of the system. The photocurable polymer can be formulated into useful systems including in liquid resists, pre-coated film resists, etc. and can be used in both negative or positive imaging systems.

30 Claims, 4 Drawing Sheets

OTHER PUBLICATIONS

Williams, "Light-sensitive Polymeric Quaternary Salts", *Chemical Abstracts*, vol. 54, col. 4223.

Williams, "Photodimerization of 2-styrylpyridine", *The Journal of Organic Chemistry*, vol. 25, No. 11, pp. 1839–1840 (1960).

Williams et al., "Cis and Trans Isomers of 2-Styrylpyridine", *Journal of Organic Chemistry*, vol. 26, pp. 4893–4895 (1961).

Williams, "Trans-Cis-Trans- Phototropism of 2-Styrylpyridine Methiodide", *Journal of the American Chemical Society*, vol. 84, p. 1323 (1962).

Williams et al, "A Comparison of Methods for the Preparation of 2- and 4- Styrylpyridines", *Journal of Organic Chemistry*, vol. 28, pp. 387–390 (1963).

Williams et al., "The Preparation and Properties of Photoreactive Polymers", *Makromolekulare Chemi*, vol. 73, pp. 203–215 (1963).

Williams et al., "Photochemical Transformations of Some 4'-Amino-2-Styrylpyridines and their Salts", *Canadian Journal of Chemistry*, vol. 43, pp. 1345–1356 (1965).

Williams, J. L. R. "Photoreactive Polymers", *Polyelectrolytes*, pp. 507–528 (1974).

ACID SOLUBLE PHOTO-RESIST COMPRISING A PHOTOSENSITIVE POLYMER

FIELD OF THE INVENTION

The invention relates to photocross-linkable polymeric systems. More particularly, the invention relates to aqueous compositions containing solutions or dispersions of polymeric materials having a pendant group, with a basic nature in an aqueous system, having pendant styryl-amine or nitrogen heterocyclic substituents. The polymeric materials of the invention have the advantage of solubility at PH<7, insolubility at pH>7 and rapid photocross-linking. The invention also relates to photoresist compositions made from the polymer composition of the invention and from other components. The invention further relates to methods of producing the polymeric system, vinyl monomers containing the styryl-nitrogen heterocycle active group and to various methods of forming the styryl-nitrogen heterocycle group on the polymer backbone. The invention further relates to aqueous solutions, aqueous dispersions, film-like resists, printing plates, screen stencils, and methods of photoimaging using the active polymer system.

The photocross-linkable polymeric systems of the invention are useful in those photochemical processes in which photocross-linking occurs to form a latent image which may be developed with a suitable developer. These processes usually are not described as photographic processes. Photography is typically defined as the process of forming visible images directly or indirectly by the action of light or other forms of radiation on sensitive surfaces, for example, silver halide emulsions.

BACKGROUND OF THE INVENTION

Photosensitive or photoreactive polymers are commonly used in coatings which have properties that can change when exposed to light. Such a change in properties is usually a change in solubility and results in a sharp distinction between exposed and unexposed areas. Photocross-linking and photoinitiated polymerization are commonly used to exploit the photosensitivity of materials. This invention relates to photocross-linking between ethylenically unsaturated sites. Exposure to light of the photosensitive or photoreactive material results in a solubility change and creation of image in the resist material. Most commonly, images are produced by solvent development, either negative or positive modes. Photoresist polymer compositions must fill a number of physical property dependent requirements under practical working conditions. The most important, and most difficult, requirements to fulfill is image discrimination, thermal stability, ink resistance, and etch resistance when exposed. For image discrimination, the developing solvent must remove the soluble portion of the exposed imagery without distorting or swelling the insoluble areas to give a sharp, true image. In the past, resist polymers were required only to withstand liquid aqueous etchants, for example, ammonia fluoride, hydrofluoric acid, etc. However, present trends towards other etching modes require polymers with a variety of properties.

Most commonly, photomodification of polymer functionality depends on the modification of the solubility of polymer-bound chromophore units upon light absorption. A change in functionality modifies the solubility of the polymer through pendant groups in selected solvents. For example, with sufficient exposure to light, a polymer having diazo ketone units becomes hydrophilic. A variety of photo-chemical systems have been used in photoresist applications including cinnamates, chalcones, p-azidophenyls, azidophthalates, p-phenylene, bis(acrylates), etc. One class of compounds used in forming photoinitiated dimerization is set forth in references including K. Ichimura, J. Poly. Sci. 20, 1411, 1982; K. Ichimura, et al., J. Poly. Sci. 20, 1419, 1982; Ichimura, et al., U.S. Pat. No. 4,777,114 (1988); U.S. Pat. No. 4,564,580 (1986); European Patent No. 130 804 (1984); Japanese Patent No. 63/198045 (1988); Balfour, European Patent No. 313 221 (1989); Sperry, European Patent No. 092 901 (1983); etc.

This technology involves using an aldol-type condensation reaction to graft a photodimerizable group onto a polyvinyl alcohol backbone as shown in a cross-linked and uncross-linked form.

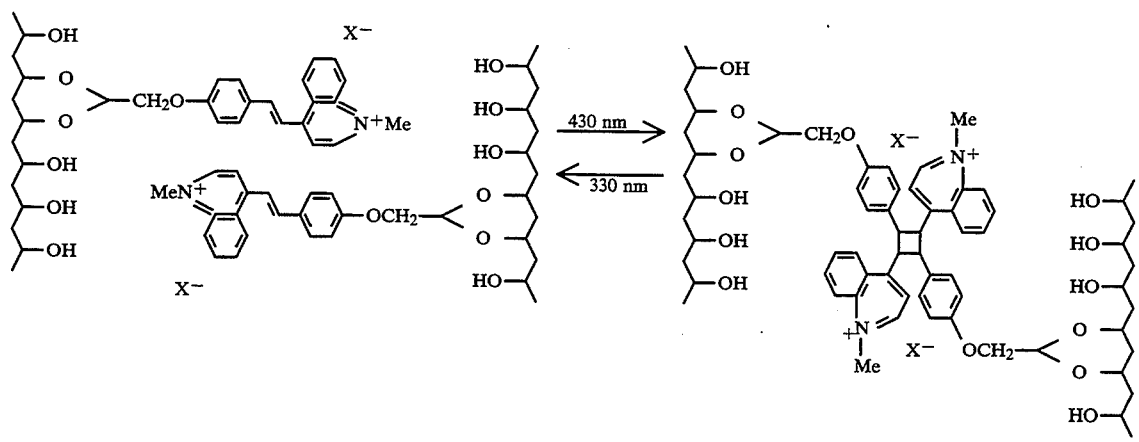

Unfortunately, the Ichimura, et al. technology suffers from the following drawbacks: (1) the materials remain water sensitive at any pH due to residual unreacted polyvinyl alcohol functionality and (2) the materials are expensive.

Other water sensitive or water soluble polymeric materials are disclosed in Mukunoki et al., U.S. Pat. No. 4,917,993, which discloses the use of a particular class of water soluble synthetic or natural polymers in silver halide photographic materials. The synthetic polymers disclosed in Mukunoki preferably have nonionic and/or anionic groups appended onto a poly(methyl) backbone which may or may not be otherwise substituted. These appended groups are linked to the poly(methyl) backbone through the following oxygen-containing linking groups: —CONH—, —NHCO—, —COO—, —OCO—, or —O—.

In order to satisfy the increasing demands for more versatile photoresist materials, we have sought to develop photoreactive or photosensitive polymers that satisfy demands in the art. Useful screen printing inks must be adherent to the substrate, uniform in drying, and exhibit thixotropic flow. In systems which are water-resistant, more specifically, water-based ink resistant, the stencil must exhibit controlled water solubility and cross-linkability. In other words, the materials should have properties that aid in controlling the water solubility of the polymer system. The materials, under use conditions, should be water soluble when unexposed and water resistant when exposed. The materials, after exposure, which must be removed, must be rendered sensitive to water, i.e., capable of selective or controlled dispersion or dissolution in order to remove or reclaim the photosensitive stencil or photoresist. We have found that pH sensitivity of the photoresist can be used as a primary tool for attaining the above listed goals. We have found that basic (pH>7 or alkaline reacting) photo-polymers enable us to achieve the goals set forth above. Using acid solubilization, the unexposed photopolymers are inherently water soluble and are easily formulated and used in aqueous solutions. However, in alkaline or basic aqueous solutions, the materials can be quite insoluble resulting in a waterresistant stencil formed on a substrate. After adequate cross-linking, the formed image, either positive or negative, has substantial solvent resistance (aqueous and organic) in both acid and basic solution.

Therefore, a polymer having pendant basic insoluble and acid soluble photocross-linking groups in a photosensitive system would satisfy the requirements and constraints set forth above for photosensitive stencil products that can be formulated in a liquid or a pre-cast film for positive and negative imaging.

BRIEF DESCRIPTION OF THE INVENTION

We have found that the pH properties discussed above can be attained through the formation of a polymeric material having a poly(methyl) backbone and pendant groups formed from a basic amine group. The polymer may be a homo-, co-, or terpolymer. The material also contains a photocross-linking group comprising a styryl-amine or styryl-heterocyclic nitrogen group. The basic nature of the pendant amine groups in aqueous solution provides the acid solubility and basic insolubility properties. The styryl-amine or styryl-heterocyclic group provides an ethylenically unsaturated dimerization site. A dimerization site from each of two polymer chains can cooperate in a photocross-linking insolubilization to form a cyclobutane cross-link which bridges the two polymer chains.

We have found that the water-based polymer materials obtain excellent adhesion to a substrate. Solvents may enhance adhesion of the polymeric material to the substrate when employing through an aqueous-based material, but when the composition dries to form a film, the solvents evaporate and do not add to the weight of the photosensitive coating. The aqueous materials containing water and other compatible soluble or dispersible materials dry uniformly, have controlled evaporation rates, and form uniform, polymer films. Thickeners and thixotropes can be used in the aqueous compositions to modify rheological properties. The polymeric materials of the invention have the following advantages: (1) precise control over photocross-linking using the styryl-heterocyclic pendant groups and (2) aqueous processing capability wherein the polymeric composition has differential solubility with changing pH.

In somewhat greater detail, we have found that the pH-sensitive properties of the polymeric material are important. Using a photopolymer exhibiting the properties of a base, we have found that photosensitive systems can be constructed to have the advantages discussed above. The polymeric material can be formed as a nitrogen-containing basic material and solubilized in an acidic solution. In addition, the photopolymer may be formulated having quaternized nitrogen atoms in groups pendant to the polymeric chain wherein the polymer is inherently water soluble. The alkaline (aqueous base) nature of the material can be made fully insoluble if the material is neutralized or introduced into a basic environment. Lastly, photocross-linking can result in substantial solvent resistance.

By "pH sensitivity" we mean that the polymer is soluble in acidic aqueous environments and is insoluble in alkaline or basic aqueous environments.

By "polymer" we mean to include photosensitive polymers having amino groups as well as quaternized salts thereof.

DETAILED DESCRIPTION OF THE INVENTION

Figure 1A:
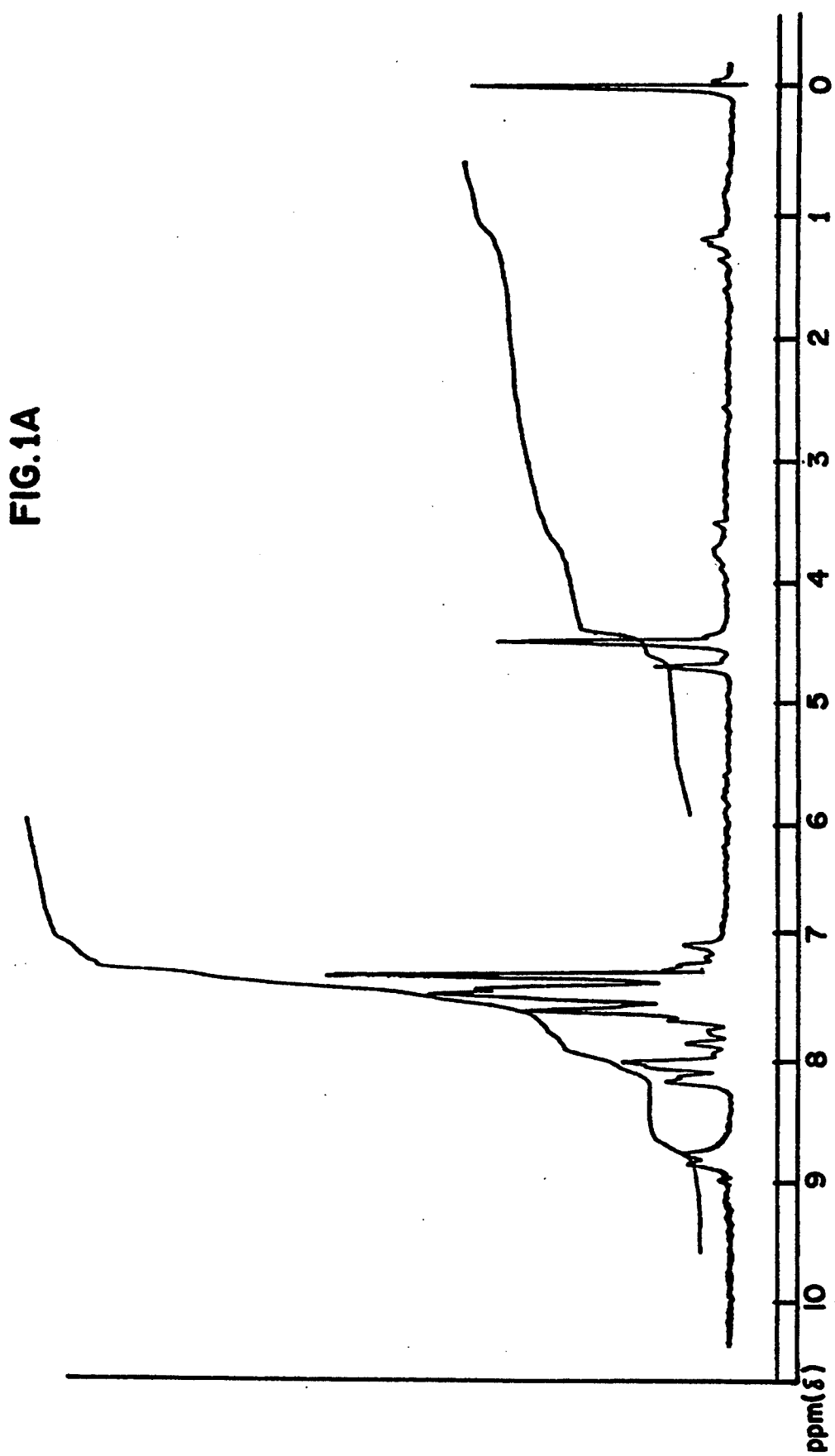
FIGS. 1A and 1B represent graphs of the result of NMR spectrometry of 4-[2-(4-chloromethylphenyl)ethenyl] quinoline which may be used in the practice of our invention.

The polymeric material of our invention comprises a poly(methyl) backbone and pendant groups formed from a basic amine group and from a photosensitive group comprising a styryl-amine or heterocyclic nitrogen group. The portion of the poly(methyl) backbone and the pendant photosensitive group is shown in the following structure:

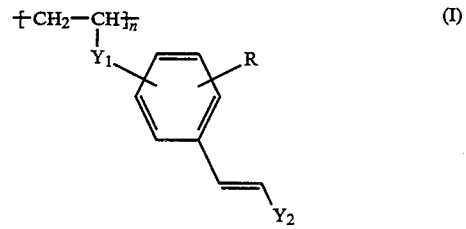

wherein R is hydrogen, alkyl (preferably $C_{1-6}$ branched or unbranched alkyl), alkoxy, aldehyde, carboxyl, oxy, hydroxyl, aryl, aryloxy, halo, cyano, amino, etc.; $Y_1$ comprises an amine moiety, a heterocyclic nitrogen-containing organic moiety having about 1 to 26 carbon atoms linked through the atoms of the heterocycle, or an heterocyclic nitrogen-containing organic moiety having about 1 to 26 carbon atoms linked through at least one $C_{1-6}$ alkyl substituent; and $Y_2$ comprises an amine moiety or a heterocyclic nitrogen-containing organic moiety having about 1 to 26 carbon atoms. The photosensitive polymer generally has a molecular weight of about 1,000 to 1,000,000. The polymer can be a homopolymer comprising repeating units of formula (I), or it can be a co- or terpolymer comprising repeating units of formula (I) and other monomeric units.

The pH sensitivity and cross-linkability of the polymer material of the invention is derived from both the pendant amine groups and from the styryl-heterocyclic pendant groups illustrated in the following structure:

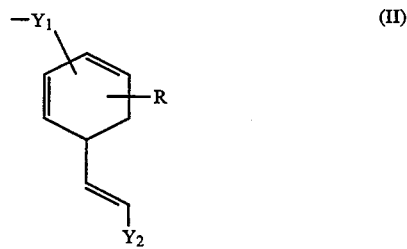

(II)

wherein R is hydrogen, alkyl, alkoxy, aidehyde, carboxyl, oxy, hydroxyl, aryl, aryloxy, halo, amino, cyano, etc. and $Y_1$ and $Y_2$ independently comprise an amine moiety or a heterocyclic nitrogen-containing group, such as a substituted or unsubstituted pyridinium salt, a substituted or unsubstituted quinolinium salt, a substituted or unsubstituted benzothiazolinium salt, etc., or $Y_1$ can comprise a heterocyclic nitrogen-containing group as outlined above which is linked through at least one $C_{1-6}$ alkyl substituent.

Such pH sensitive, photocross-linkable pendant groups can be formed onto a poly(methyl) backbone by forming a vinyl monomer having the pH sensitive pendant group having ethylenic unsaturation in a styryl group illustrated below:

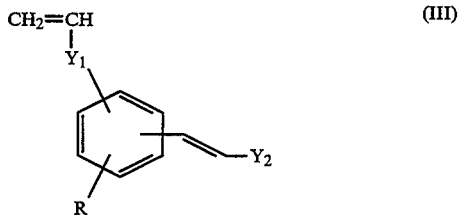

(III)

wherein R is hydrogen, alkyl, alkoxy, aidehyde, carboxyl, oxy, hydroxyl, aryl, aryloxy, halo, cyano, amino, etc.; $Y_1$ comprises an amine moiety, a heterocyclic nitrogen-containing organic moiety having about 1 to 26 carbon atoms linked through the atoms of the heterocycle, or an heterocyclic nitrogen-containing organic moiety having about 1 to 26 carbon atoms linked through at least one alkyl substituent; and $Y_2$ comprises an amine moiety or a heterocyclic nitrogen-containing organic moiety having about 1 to 26 carbon atoms. The monomer may then be polymerized to form a vinyl polymer, having the pendant pH sensitive cross-linkable groups. The vinyl monomer may be homopolymerized or can be co- or terpolymerized with common ethylenically unsaturated vinyl monomers to form useful polymeric solutions or dispersions.

Photosensitive Pendant Group

The photosensitive pendant group, formula (II), illustrated above is generally a modification of the photosensitive group "SBQ" taught in K. Ichimura, J. Poly. Sci. 20, 1411, 1982; K. Ichimura, et al., J. Poly. Sci. 20, 1419, 1982; Ichimura, et al., U.S. Pat. No. 4,777,114 (1988); U.S. Pat. No. 4,564,580 (1986); European Patent No. 310 804 (1984); Japanese Patent No. 63/198045 (1988); the disclosure of these references is herein incorporated by reference. However, any basic photosensitive functionality which can be appended to the poly(methyl) backbone could be used in our system. Again, the pH sensitive pendant group comprises a styryl moiety and has the general structure:

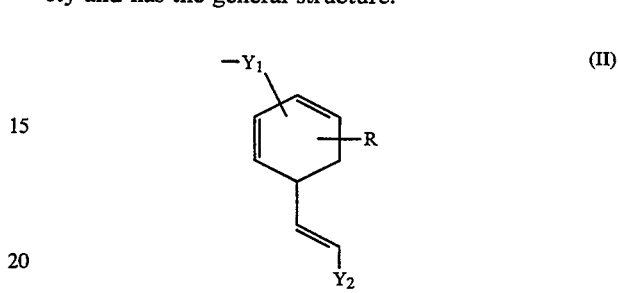

(II)

wherein R is hydrogen, alkyl, alkoxy, aidehyde, carboxyl, oxy, hydroxyl, aryl, aryloxy, halo, amino, cyano, etc.; and $Y_1$ and $Y_2$ independently comprise an amine moiety or a heterocyclic nitrogen-containing group, such as a substituted or unsubstituted pyridinium salt, a substituted or unsubstituted quinolinium salt, a substituted or unsubstituted benzothiazolinium salt, etc.; or $Y_1$ can comprise a heterocyclic nitrogen-containing group as outlined above which is linked through at least one $C_{1-6}$ alkyl group.

In greater detail the $Y_1$ linking group may be any basic amino group which may be grafted onto a poly(methyl) polymer backbone or which may be reacted with ethylene to result in vinyl functionality or a derivative thereof. A representative, non-limiting list of such groups includes derivatives of heterocyclic compounds including $C_{1-6}$ alkyl substituted derivatives thereof such as benzothiazole, morpholine, oxazole, isoxazole, piperazine, piperidine, purine, pyrazine, pyridine, pyrimidine, quinazoline, quinoline, quinoxazoline, and tetrazole; alkylamines wherein the alkyl group is directly bonded to the amino group such as linear, branched and cyclic $C_{1-12}$ amines, methylamine, isopropylamine, and cyclohexylamine; and arylamines wherein the aryl group is directly bonded to the amino group such as aniline, phthalimide, and benzyl amine. Preferably, the nitrogenous base is bonded to the styryl moiety through a quaternary nitrogen atom or through a direct covalent bond to a heterocyclic or aryl ring carbon or an alkyl substituent of the amine or amino compound.

In addition, the ring of the styryl moiety may be substituted or unsubstituted. However, any substitution of the styryl moiety should not defeat the overall basic nature of the pendant group. Such substitution may include hydrogen, alkyl, alkoxy, aidehyde, carboxyl, oxy, hydroxyl, halo, aryl, aryloxy, amino, cyano, etc. Preferably, the styryl moiety is unsubstituted.

The $Y_2$ group may be any basic nitrogen-containing moiety which may be linked to a styryl group. A representative, non-limiting list of such groups includes derivatives of heterocyclic compounds such as benzothiazole, morpholine, oxazole, isoxazole, piperazine, piperidine, purine, pyrazine, pyridine, pyrimidine, quinazoline, quinoline, quinoxazoline, and tetrazole; alkylamines wherein the alkyl group is directly bonded to the amino group such as linear, branched and cyclic $C_{1-12}$ amines, methylamine, isopropylamine, and cyclohexylamine; and arylamines wherein the aryl group is directly bonded to the amino group such as aniline, phthalimide, and benzyl amine. Preferably, the nitrogen base $Y_2$ comprises at least one quaternary nitrogen atom. More preferably, the nitrogen base $Y_2$ comprises a heterocyclic quaternary ammonium compound.

The pendant group may grafted onto a polymeric chain or the pendant group or a part thereof may be reacted with another compound to form a vinyl monomer and polymerized, copolymerized, or terpolymerized to form the photosensitive polymer of our invention. In one manner of making the photosensitive polymer, the majority of the pendant group is formed and then grafted onto a polymeric backbone comprising the $Y_1$ linking group. A variety of reaction sequences can be used to form the pendant photosensitive group. The pendant moiety may be synthesized through the following reaction sequence:

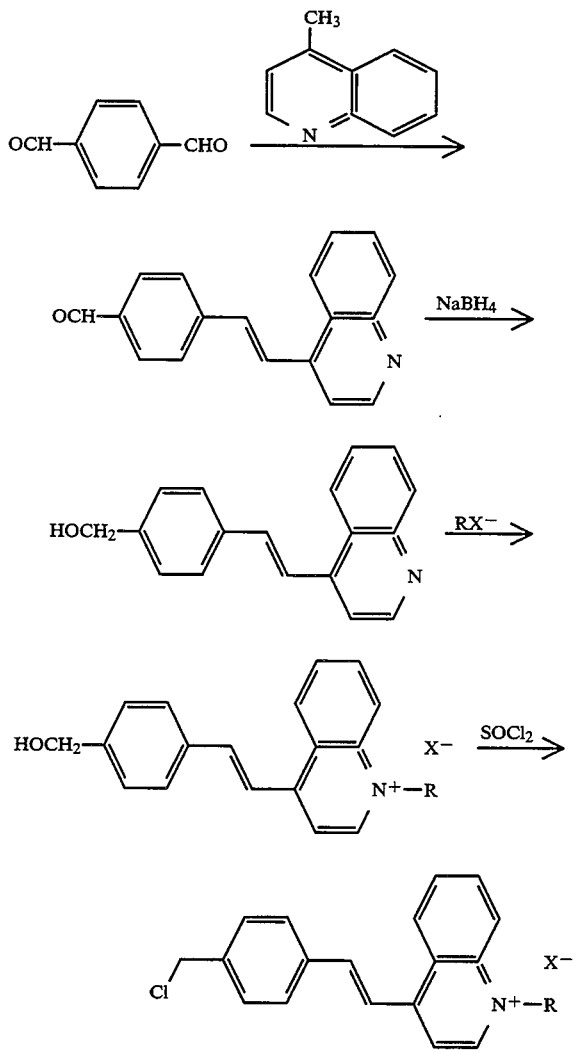

wherein R=Me or H; $X^-=I^{31}$ or $MeOSO_3^-$. Of course, the exemplary material can be genericized to a variety of reactive species. Indeed, a number of other syntheses and reagents may be used to form a pendant group without departure from the spirit of our invention.

As discussed above, the $Y_1$ and $Y_2$ groups are generally amino groups or amino derivatives. Preferably, the amino moieties comprise quaternary ammonium moieties. Indeed, the nitrogenous base is bonded to the styryl moiety through a quaternary nitrogen atom or through a direct covalent bond to a heterocyclic or aryl ring carbon or an alkyl substituent of the amine or amino compound. This character of the pendant group contributes to the water soluble nature of the polymer in an uncross-linked state. The $Y_1$ and $Y_2$ groups are preferably nitrogen-containing heterocyclic rings. More preferably, the groups are pyridine or quinoline derivatives, and most preferably, they are pyridinium or quinolinium salts.

The basic functionality of the $Y_1$ and $Y_2$ groups helps to give the resulting polymer characteristics of acid solubility and basic insolubility. This allows the excellent control of the application and removal of a polymeric film comprising the photosensitive polymer simply by controlling the pH of the liquids which contact the polymeric film. Further, the basic insolubility allows the polymeric film to exhibit increased resistance to attack by printing inks, many of which are alkaline. Thus, the increased basic nature of the photosensitive polymer of which we have developed is an important improvement in the art.

The pendant group of the photosensitive polymer provides ethylenic unsaturation in the photopolymer which can be cross-linked to an adjacent pendant group of an adjacent photopolymer upon exposure to light. Further, this cross-linking can be reversible as disclosed in K. Ichimura, J. Poly. Sci. 20, 1411, 1982. Thus, our polymeric film can be applied to a substrate, exposed in a selective manner to light of a particular frequency to cross-link those exposed areas, contacted with an acidic aqueous composition to remove the unexposed areas, used as a mask, exposed to a second frequency of light to cleave the photocross-linked polymers, and again contacted with an acidic aqueous composition to remove the polymeric film.

pH and Photosensitive Monomer

The monomer of our invention has two basic nitrogenous moieties, an internal styryl moiety and a terminal vinyl group and is illustrated below:

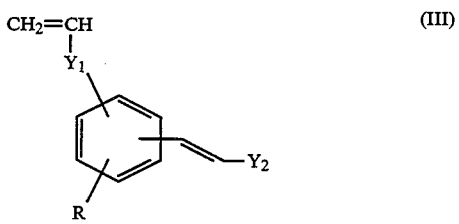

wherein R is hydrogen, alkyl, alkoxy, aldehyde, carboxyl, oxy, hydroxyl, aryl, aryloxy, halo, cyano, amino, etc.; $Y_1$ comprises an amine moiety, a heterocyclic nitrogen-containing organic moiety having about 1 to 26 carbon atoms linked through the atoms of the heterocycle, or an heterocyclic nitrogen-containing organic moiety having about 1 to 26 carbon atoms linked through at least one $C_{1-6}$ alkyl substituent; and $Y_2$ comprises an amine moiety or a heterocyclic nitrogen-containing organic moiety having about 1 to 26 carbon atoms.

The vinyl monomer generally has the characteristics of the pH and photosensitive pendant group discussed above. In addition, the terminal ethylenic unsaturation provides an excellent polymerization site.

The vinyl photosensitive monomer can be homo-, co-, or terpolymerized to form a photopolymer. However, the polymerization should result in a photopolymer which has significant basic properties. In other words, the polymerization should not detrimentally affect the acid solubilization and alkaline insolubilization of the polymer. The photosensitive monomer can be co- or terpolymerized with a wide variety of comonomers provided that the comonomers do not detrimentally affect the acid solubilization, alkaline insolubilization, and photocrosslinkability of the resulting copolymer. A representative, non-limiting list of potential comonomers includes heterocyclic vinyl monomers such as vinylimidazole, 2-methyl-1-vinylimidazole, vinylpyridine, vinylpyrimidine, vinylquinoline, or derivatives thereof; other vinyl monomers such as vinylacetate (followed by saponification to vinylalcohol), vinylsuccinimide, styrene, vinyl esters, vinyl ethers, vinyl halides, vinyl methyl ether, vinylidene chloride, and vinyl chloride; acrylates such as methyl acrylate, hydroxyethylacrylate, methyl methacrylate, hydroxy propylacrylate, 2-ethylhexylacrylate, and butylacrylate; acrylamides such as N-methylolacrylamide and methyl acrylamide; unsaturated carboxylic acids and salts thereof such as acrylic acid, methacrylic acid, crotonic acid, fumaric acid, iraconic acid, and maleic acid; and monomers used in cationic polymerization such as dialkylaminoethyl methacrylates, isobutene, styrene, and α-methyl styrene. The polymers, copolymers, and terpolymers of our invention can yield performance characteristics to meet many applications. The skilled practitioner will recognize the balancing of comonomers to achieve desired properties such as flexibility, solution viscosity, imaging properties, stencil characteristics (resolution, durability, processing, etc.), and development rate.

pH Sensitive Photopolymer

Again, the polymeric material of our invention comprises a poly(methyl) backbone and pendant groups formed from a basic group and a photosensitive group comprising a styryl-amine or heterocyclic nitrogen group as shown in the following structure:

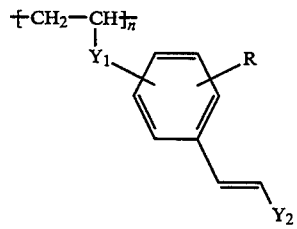

(I)

wherein R is hydrogen, alkyl, alkoxy, aidehyde, carboxyl, oxy, hydroxyl, aryl, aryloxy, halo, cyano, amino, etc.; $Y_1$ comprises an amine moiety, a heterocyclic nitrogen-containing organic moiety having about 1 to 26 carbon atoms linked through the atoms of the heterocycle, or an heterocyclic nitrogen-containing organic moiety having about 1 to 26 carbon atoms linked through at least one $C_{1-6}$ alkyl substituent; $Y_2$ comprises an amine moiety or a heterocyclic nitrogen-containing organic moiety having about 1 to 26 carbon atoms; and the photosensitive polymer has a molecular weight of about 1,000 to 1,000,000. Of course, the polymer may comprise additional pendant groups. It is important that a significant number of these pendant groups have a basic nature to give the polymer its pH sensitivity.

Indeed, the polymer may be a copolymer having the general formula:

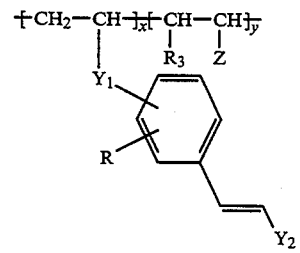

wherein x is about 0.1 to 100 mole-%, preferably about 0.1 to 20 mole-%; y is about 0 to 99.9 mole-%, preferably about 80 to 99.9 mole-%; R and $R_3$ can be independently hydrogen, $C_{1-6}$ branched or unbranched alkyl, alkoxy, carboxyl, aryl, aryloxy, halo, cyano, or amino; $Y_1$ comprises an amine moiety, a heterocyclic nitrogen-containing organic moiety having about 1 to 26 carbon atoms linked through the atoms of the heterocycle, or an heterocyclic nitrogen-containing organic moiety having about 1 to 26 carbon atoms linked through at least one $C_{1-6}$ alkyl substituent; $Y_2$ comprises an amine moiety or a heterocyclic nitrogen-containing organic moiety having about 1 to 26 carbon atoms; Z comprises hydrogen, alkyl, ester, alkoxy, aidehyde, carboxyl, oxy, hydroxyl, aryl, aryloxy, halo, cyano, amino, or a heterocyclic nitrogen-containing organic moiety having about 1 to 26 carbon atoms; and the photosensitive polymer has a molecular weight of about 1,000 to 1,000,000. The copolymer may be either a random or block copolymer.

A preferred class of copolymeric photopolymers has the general formula:

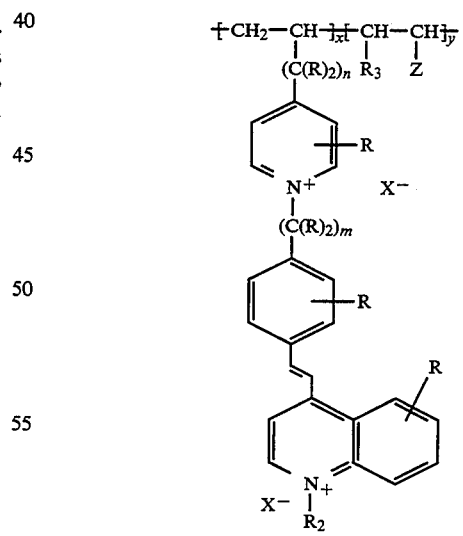

wherein each R and $R_3$ are independently hydrogen, $C_{1-6}$ branched or unbranched alkyl, alkoxy, aidehyde, carboxyl, oxy, hydroxyl, aryl, aryloxy, halo, cyano, or amino; $R_2$ is hydrogen or a $C_{1-12}$ branched or unbranched alkyl group; x is about 9.5 to 20 mole-%; y is about 99.5 to 80 mole-%; m and n are independently about 0 to 6; $X^-$ is an anion selected from the group consisting of halide, alkyl sulfate, alkyl sulfonate, alkyl phosphate, alkyl hexaphosphate, alkyl phosphonate, or boron tetrafluoride; Z is $C_{1-4}$ alkyl, carboxylic, aryl, benzyl, halo, an amine moiety, or a heterocyclic nitrogen-containing organic moiety having about 1 to 26 carbon atoms; and the photosensitive polymer has a molecular weight of about 1,000 to 1,000,000. More preferably, either m or n is about 1 to 6, and most preferably, m is about 1 to 6. The photopolymers in which m is at least one have the benefit of being more readily synthesized using currently known techniques.

In addition, the copolymeric photopolymer may be a terpolymer having the general formula:

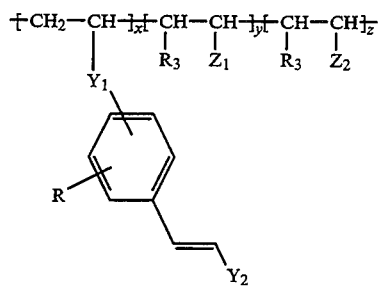

wherein x is about 0.1 to 100 mole-%, preferably about 0.1 to 20 mole-%; y is about 0 to 99.9 mole-%; z is about 0 to 99.9 mole-%; each R and $R_3$ can be independently hydrogen, $C_{1-6}$ branched or unbranched alkyl, alkoxy, carboxyl, aryl, aryloxy, halo, cyano, or amino; $Y_1$ comprises an amine moiety, a heterocyclic nitrogen-containing organic moiety having about 1 to 26 carbon atoms linked through the atoms of the heterocycle, or an heterocyclic nitrogen-containing organic moiety having about 1 to 26 carbon atoms linked through at least one $C_{1-6}$ alkyl substituent; $Y_2$ comprises an amine moiety or a heterocyclic nitrogen-containing organic moiety having about 1 to 26 carbon atoms; $Z_1$ and $Z_2$ independently comprise an amine moiety, a heterocyclic nitrogen-containing organic moiety having about 1 to 26 carbon atoms, hydrogen, $C_{1-4}$ alkyl, carboxylic acid, ester, and the photosensitive polymer has a molecular weight of about 1000 to 1,000,000. Again, the polymer may be a random or block terpolymer.

A representative, non-limiting list of potential comonomers includes heterocyclic vinyl monomers such as vinylimidazole, 2-methyl-1-vinylimidazole, vinylpyridine, vinylpyrimidine, vinylquinoline, or derivatives thereof; other vinyl monomers such as vinylacetate (followed by saponification to vinylalcohol), vinylsuccinimide, styrene, vinyl esters, vinyl ethers, vinyl halides, vinyl methyl ether, vinylidene chloride, and vinyl chloride; acrylates such as methyl acrylate, hydroxyethylacrylate, methyl methacrylate, hydroxy propylacrylate, 2-ethylhexylacrylate, and butylacrylate; acrylamides such as N-methylolacrylamide and methyl acrylamide; unsaturated carboxylic acids and salts thereof such as acrylic acid, methacrylic acid, crotonic acid, fumaric acid, itaconic acid, and maleic acid; and monomers used in cationic polymerization such as dialkylaminoethyl methacrylates, isobutene, styrene, and α-methyl styrene.

The photopolymer can be synthesized through the homo or copolymerization of the monomer as described above, or it can be synthesized by grafting a photosensitive group onto a polymer. Preferably, the photopolymer is formed through the grafting of a photosensitive moiety onto a polymer through a nitrogenous organic moiety, e.g., $Y_1$ of formula (I). Such moiety must contain at least one active site or site which can be activated which can react with the group forming the pendant basic photocross-linkable member. The linkage may be through a quaternary nitrogen atom, through any heterocyclic ring member, or through $C_{1-6}$ alkyl substituents of a heterocycle. It is preferred that the nitrogen organic moiety is linked to the photocross-linkable group through a quaternary nitrogen atom. A variety of nitrogen alkalization reactions can be used to form the quaternary nitrogen group. The following general reaction sequence can be used for forming the photopolymer of the invention. This exemplary material can be genericized to a variety of reactive species. In a first step, 4-(bromomethyl)-benzaldehyde is reacted with a polyvinyl pyridine polymer wherein the bromomethyl group quaternizes the pyridine nitrogen as shown in the following reaction sequence:

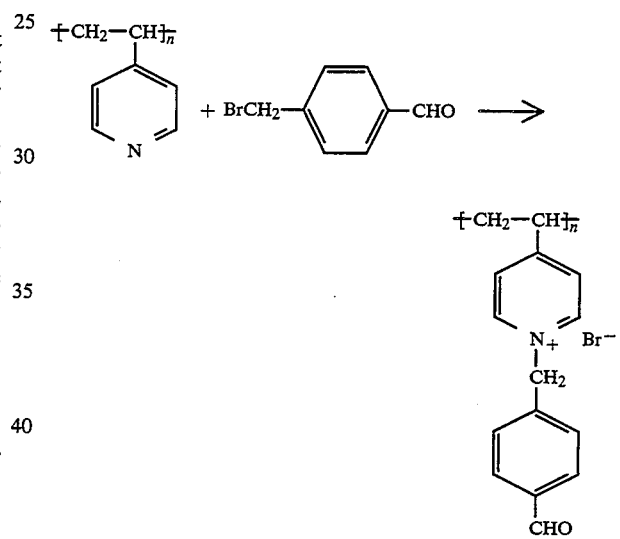

wherein n is from about 5 to about 25,000. The aldehyde functionality on the resulting pendant group can be further reacted with the substituted nitrogen heterocycle to form the styryl-nitrogen heterocycle pendant group as exemplified in the following reaction sequence:

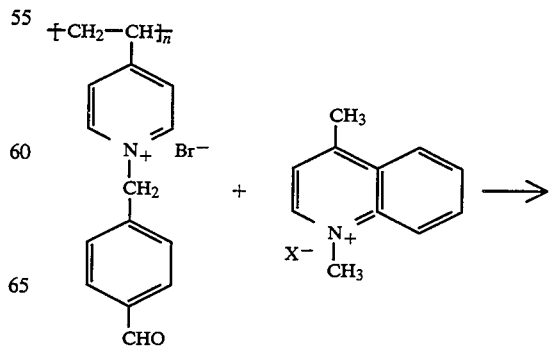

-continued

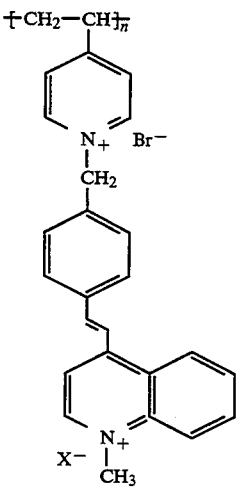

wherein $X^- = I^-$ or $MeOSO_3^-$, resulting in a fully-formed basic photocross-linkable group. It should be apparent from the above reaction sequences that the initial polymeric reactant can be formed from a variety of nitrogenous bases. Further, the intermediate reaction step can be performed using a variety of nitrogen alkylating agents having the free aldehyde group. Finally, the last step forming the styryl-heterocyclic substituent can involve a variety of methyl-substituted heterocyclic quaternary materials.

In addition, the photosensitive moiety can be grafted as a whole onto the polymeric backbone through a pendant nitrogen-containing organic moiety. In this manner, a pendant group according to formula (II) can be grafted onto a polyvinylpyridine backbone as shown below:

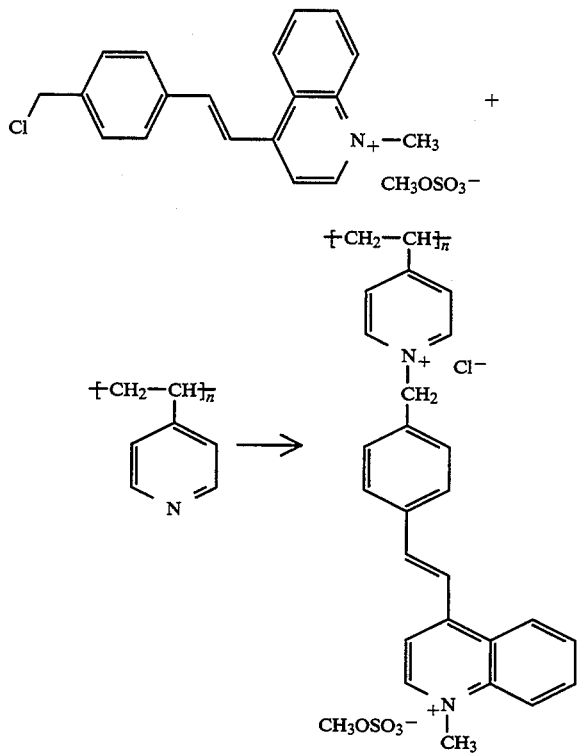

Of course a number of other syntheses and reagents may be used to form photopolymers of our invention without departure from the spirit of our invention.

With any of the above described photopolymer synthesis procedures, the quaternary nitrogen group (if any), the ethylenically unsaturated portion of the styryl group, and the aromatic rings of the pendant group cooperate to produce the cross-linkability of the pendant group. The cross-linkage occurs through the ethylenically unsaturated moiety which can form cyclobutane groups when reacted with adjacent ethylenically unsaturated groups on an adjacent polymer chains.

The photopolymers useful in the photoresists of the invention can have a molecular weight of about 1,000 to 1,000,000. At the lower end of the range, the photopolymers may actually be oligomers. At a molecular weight of about 1,000,000, the photopolymers may be cast as films from a melt of about 100% solids. Of course, if the molecular weight is too low, polymerization and photo-cross-linking may be ineffective to render the material insoluble after imaging and developing. If the molecular weight is too great, the viscosity of an aqueous solution or resin melt may be too high for handling. More preferably, the molecular weight ranges from about 10,000 to 500,000. This range is generally more forgiving, i.e., the formulator has the opportunity to vary composition proportions to balance viscosity, solubility rate, pliability, ductility, etc. Most preferably, the polymer has a molecular weight of about 20,000 to 250,000. This range generally is the most versatile and economically viable.

Of course, the ordinary practitioner may desire or need to formulate the photopolymer to meet specific needs. The viscosity of the photoresist composition generally results from a balance of % solids in a solution or dispersion and the molecular weight of the polymer. Increasing either the % solids or the molecular weight generally results in increased viscosity. In addition, as the molecular weight increases it may be necessary to decrease the cross-linkability of the photopolymer so it remains soluble or dispersible in the developer. High viscosity dispersions may be useful to achieve thicker photoresist films and to reduce their cold flow and tack. The incorporation of lower molecular weight polymers or oligomers either as the source of polymers or as a reactive diluent may render the photoresist or stencil harder and more brittle which can be desireable to enhance performance under certain conditions.

The photopolymers of our invention can be used in various forms to provide photosensitive screens, masks, stencils, etc., for use in both negative and positive photoimaging systems. These photoimaging systems develop latent images prior to developing and are typically non-silver halide systems. The photopolymer may be used as a flexible resist or printing plate. The photopolymers may also be used as a liquid photoresistant composition comprising a proportion of a liquid carrier and about 0.1 to 100 wt-% of a photosensitive polymer (or photopolymer) of our invention. Such uses are known to those of ordinary skill in the art. For example, descriptions of these uses are disclosed in Ichimura et al., U.S. Pat. No. 4,567,580, and Van Iseghem, U.S. Pat. No. 4,764,449; the disclosures of both are herein incorporated by reference. Preferably, the liquid composition comprises the liquid carrier and about 1 to 60 wt-% of the photopolymer.

The liquid composition is generally a solution or a dispersion of the photopolymer in the liquid carrier. This can take the form of an aqueous solution, an emulsion, an organic solution, or other dispersions or solutions used by those of ordinary skill in the art. The liquid carrier may be water or otherwise aqueous in nature, e.g., an aqueous acidic solution, or it may be an organic solvent or an organic liquid bulk phase in an emulsion or dispersion.

Other components which do not detrimentally affect the pH and photosensitive nature of the photopolymer to an extent to defeat its operability can be compounded or added to the material of such a photoresist film. Optional components of the photoresist film may include plasticizers, surfactants, defoaming agents, photoinitiators, fillers, reinforcing media, pigments or dyes, antioxidants, and other materials which impart desired properties to the photosensitive material of our invention. Further, the photoresist film can take the form of a screen printing stencil if applied to a screen mesh useful in such operations.

The photoresist composition can contain virtually any plasticizer that is compatible with the photo crosslinkable polymer composition and the film-forming binder polymeric composition, in the aqueous suspension. Both monomeric and polymeric plasticizers can be used in the resist composition. Monomeric plasticizers are typically plasticizers comprising small molecules having a molecular weight of less than about 1,000. Polymeric plasticizers are typically polymeric compounds commonly with molecular weights greater than about 1,000. Typical monomeric plasticizers include dialkyl adipates, dialkyl azylates, dialkyl benzoates, dialkyl citrates, dialkyl derivatives of phthalic anhydride and isophthalic anhydride, alkyl sebacates, alkyl stearate, dialkyl terephthalate, trialkyl ester of trimelitic anhydride, etc. Polymeric plasticizers include the various polyglycols and derivatives thereof, epoxy derivatives of stearate esters, or phthalate esters, and polyester plasticizers such as SANTICIZER and PARAPLEX plasticizers.

Sensitizers commonly used in photo polymerizable resist compositions are monomers having photo sensitive ethylenically unsaturated groups such as vinyl, acryloyl, methacryloyl, allyl, vinyl ether, acrylamide, etc. groups or prepolymers thereof having an average degree of unsaturation of about 1 to 5. Examples of sensitizers having a single ethylenically unsaturated group include acrylamide, acrylic acid, methacrylic acid, methyl methacrylate, and methylol acrylamide, etc. Preferred polyfunctional sensitizers have two or more photo sensitive ethylenically unsaturated groups including sensitizers such as pentaerythritol triacrylate, pentaerythritol tetraacrylate, pentaerythritol trimethacrylate, pentaerythritol tetramethacrylate, 2,2,-dibromo methyl, 1,3-propane diacrylate, triallyl isocyanurate, N,N'-methylene bis-acrylamide, and prepolymers thereof. The most preferred sensitizer comprises pentaerythritol triacrylate. Polymerization reaction initiators suitable for use in the invention are those materials which will easily generate free radicals upon exposure to heat or ultraviolet radiation. Examples of these initiators include benzoin-alkyl ethers, Michler's ketone, ditertiary butyl peroxide, dibenzothiazollyl-disulfide, dibromoacetophenone, anthroquinone, azobisisobutyronitrile, etc. In a similar fashion the ethylenically unsaturated resists of this invention can contain optional functional compounds such as defoamers, surfactants, dyes, antioxidants, perfumes, etc.

Additional optional compositions that can be used in the practice of this invention include surfactants which can be used to increase the compatibility of the aqueous resist composition with the surface of the object and to promote an even coating. A defoamer can be used to insure that the layer of resist is free of small bubbles and other foamed species. A dye can be used to permit visualization of the position and approximate thickness of the resist composition. An antioxidant can be used for the preservation of the concentrations of the crosslinking activator; and others.

The photoresist film comprising the photopolymer may be formed in any manner useful to those skilled in the art including spraying, casting, reverse or roll coating, dipping, doctor blading, etc. Other methods of use and photosensitive uses beyond those specifically disclosed herein will be recognized by the practitioner. These methods and uses of the invention are certainly within the scope of the claims appended to the end of this specification.

EXAMPLES

The following specific examples which contain the best mode, can be used to further illustrate the invention. These examples are merely illustrative of the invention and do not limit its scope.

EXAMPLE 1

Synthesis of 4-(bromomethyl)-benzaldehyde (1) 1-bromomethyl-4-dichloromethylbenzene (17 g)
(2) ethanedioic acid (6.12 g)

A mixture of starting materials (1) and (2) was melted in a 150 mL 1-neck flask and was stirred at about 120°–140° C. (oil bath) for 3.5 hours. Color of reaction mixture turned from white to brown. Reaction mixture was cooled to room temperature, dissolved in 50 ml of $CHCl_3$, filtered through a thin layer of $SiO_2$ (100 to 250$\mu$), solvent was evaporated, and residue was recrystallized from hexane (200 mL). White-yellow crystals were filtered, washed with 50 mL of petroleum ether, and dried. 6.12 g=45.9% of product was obtained. $^1$H-NMR (60 MHz) confirmed product identity. Evaporation of mother solution to 30% of original volume gave additional 4.91 g product. Total yield =11.03 g (82.8%).

EXAMPLE 2

(1) pyridine
(2) 4-(bromomethyl)benzaldehyde
(3) N-(4-formylbenzyl)pyridinium bromide
(4) N-methyl-4-methylquinolinium methosulfate (A) 10 mM of (1) was added to 5 mM of (2) without solvent. The reaction was carried out with mild heat for about 1 hour. Crystals of (3) appeared whereupon 50 ml of $Et_2O$ was added. The slurry was stirred for 30 minutes and filtered. Yield of (3)=0.550 g ($\approx$40%) (1.98 mM).

(B) To 1.98 mM of (3) in 5 mL of MeOH (abs), 2.2 mM (0.592 g) of (4) were added. No changes were observed within 3 hours of refluxing the reaction mixture. 5 drops of piperidine was added to reaction mixture, and the mixture was boiled and stirred overnight.

To an aliquot of the reaction mixture, 10 volumes of $Et_2O$ was added and the sample was placed under refrigeration. Crystals appeared, were separated, were added to the remainder of the reaction mixture, and were further diluted with ten volumes of $Et_2O$. The resulting crystals were separated and recrystallized from CHCl$_3$/petroleum ether. Yield=0.260 g (=25% yield).

The sample was then irradiated (OLITE AL 53/100, 5 kw, L1261 lamp at 40 in). UV spectra before and after irradiation were obtained: shoulder at 390 nm decreased after irradiation.

EXAMPLE 3

Synthesis of photosensitive photopolymer (1) poly(4-vinylpyridine) 20-26 wt % solution of polymer in MeOH (molecular weight=200,000)
(2) 4-(bromomethyl)benzaldehyde
(3) poly[N-(4-formylbenzyl)-4-vinylpyridinium bromide]
(4) N-methyl-4-methyl quinolininum methosulfate

TABLE I

| | (1) (mM) | (2) (mM) | (4) (mM) (30 to 50 mole % excess to (2)) |
|---|---|---|---|
| Trial A | 5 | 0.5 (0.10 g) | 0.75 (50% excess) = 0.20 g |
| Trial B | 5 | 1.5 (0.30 g) | 2.25 (50% excess) = 0.61 g |
| Trial C | 5 | 3.0 (0.60 g) | — |
| Trial D | 5 | 4.5 (0.90 g) | — |

Preparation of compound (4): 20 mM of 4-methyl-quinoline was dissolved in 5 mL of MeOH (abs) and 20.5 mM of (MeO)$_2$SO$_2$ was added. Stirring and refluxing was continued 30 minutes. After cooling 50 ml Et$_2$O was added, white precipitate was filtered and dried onto rotavap (30° C. in a bath). Yield 97%.

Reactants (1) and (2) were added together in MeOH to ultimately result in about 20-26 wt-% of (3) in MeOH in a flask as illustrated above in Table I. All reactant mixtures A through D were divided by MeOH (abs), to reduce viscosity. The mixtures were allowed to stir overnight at room temperature. It was observed that Trials C and D had formed a white rubber polymer. Addition of methanol and stirring for 1 hour did not dissolve the polymeric material.

Reactant (4) was added to flasks A and B in proportions indicated in Table I. The two flasks were stirred for 5 hours and then refluxed. The material in A had turned light green, and that in B, light yellow. IR and UV spectra confirmed that the desired materials were obtained.

A portion of the A product was used to make a film. The MeOH solvent was driven off and the film was exposed with an image for about 3 to 5 minutes to light (OLITE AL 53/100, 5 kw, L1261 lamp at 40 in). The film was then washed with water and the image appeared.

EXAMPLE 4

Synthesis of 4[2-(4-formylphenyl)ethenyl] quinoline (1) 4-[2-(4-formylphenyl)ethenyl]quinoline (1) was synthesized according to the procedure described in the *Journal of Polymer Science* 20, 1419-1432 (1982) herein incorporated by reference, using the following reactant quantities:

| 4-methyl-quinoline | 5.119 g |
|---|---|
| Terephthalaldehyde | 8.155 g |
| Xylene | 12 mL |
| ZnCL$_2$ | 0.1 g (anhydrous) |

HCl (37%) for precipitation—5 mL
Washed with benzene—3 times (3×50 mL)
5% solution of Na$_2$CO$_3$ was used (100 mL)
Crude yield=(85%)
After recrystallization (CHCl$_3$:Hexane=1:1) Yield=75% (6.8 g)
NMR (CDCl$_3$) confirmed structure

EXAMPLE 5

(1) 4-[2-(4-formylphenyl)ethenyl]quinoline (1.58g)
(2) 4-[2-(4-hydroxymethylphenyl)ethenyl]quinoline A 50 mL solution of (1) in MeOH was cooled to 0° C. and NaBH$_4$ (2 molar excess) was added. Stirring continued for 20 minutes at a temperature of about 0° to 20° C. The reaction mixture was diluted with Et$_2$O, filtered through a thin layer of SiO$_2$ and evaporated to provide a 1.59 g ($\approx$100%) yield of (2).

EXAMPLE 6

(1) 4-[2-(4-hydroxymethylphenyl)ethenyl]quinoline
(2) (MeO)$_2$SO$_2$
(3) N-methyl-4-[2-(4-hydroxymethylphenyl) ethenyl]-quinolinium methosulfate 0.2 g of (1) was mixed with 3 ml of MeOH, and 0.1 g of (2) was added at room temperature and stirred. Stirring was continued for 2 hours, solvent was partially evaporated, diluted with Et$_2$O/petroleum ether and the crystals obtained were combined on a filter. Yield of (3) =0.22 g of yellow crystals. IR, UV, NMR spectra data indicate that the desired product was obtained and that it retained its photoactivity.

EXAMPLE 7

(1) 4-[2-(4-hydroxymethylphenyl)ethenyl]quinoline
(2) 4-[2-(4-chloromethylphenyl)ethenyl]quinoline Dry crystals of (1) (1 mM) were mixed with SOCl$_2$ (0.3 mL) and immediately, a more intensive color (yellow-orange) appeared. After stirring 30 minutes, the reaction mixture was precipitated with Et$_2$O, filtered and dried in vacuo. The resulting yellow residue was mixed with a Na$_2$CO$_3$/H$_2$O solution ($\approx$5 mL), stirred 1 hour and extracted with 2-5 mL washes of CHCl$_3$, the resulting solution was dried (Na$_2$So$_4$) and evaporated. The residue (0.167 g $\approx$62%) was checked NMR ($^1$H, 60 MHz) It shows 2 singlets ($\approx$1:3) of CH$_2$OH, and CH$_2$Cl indicating that the desired product (2) was obtained. (FIG. 1A).

Figure 1B:
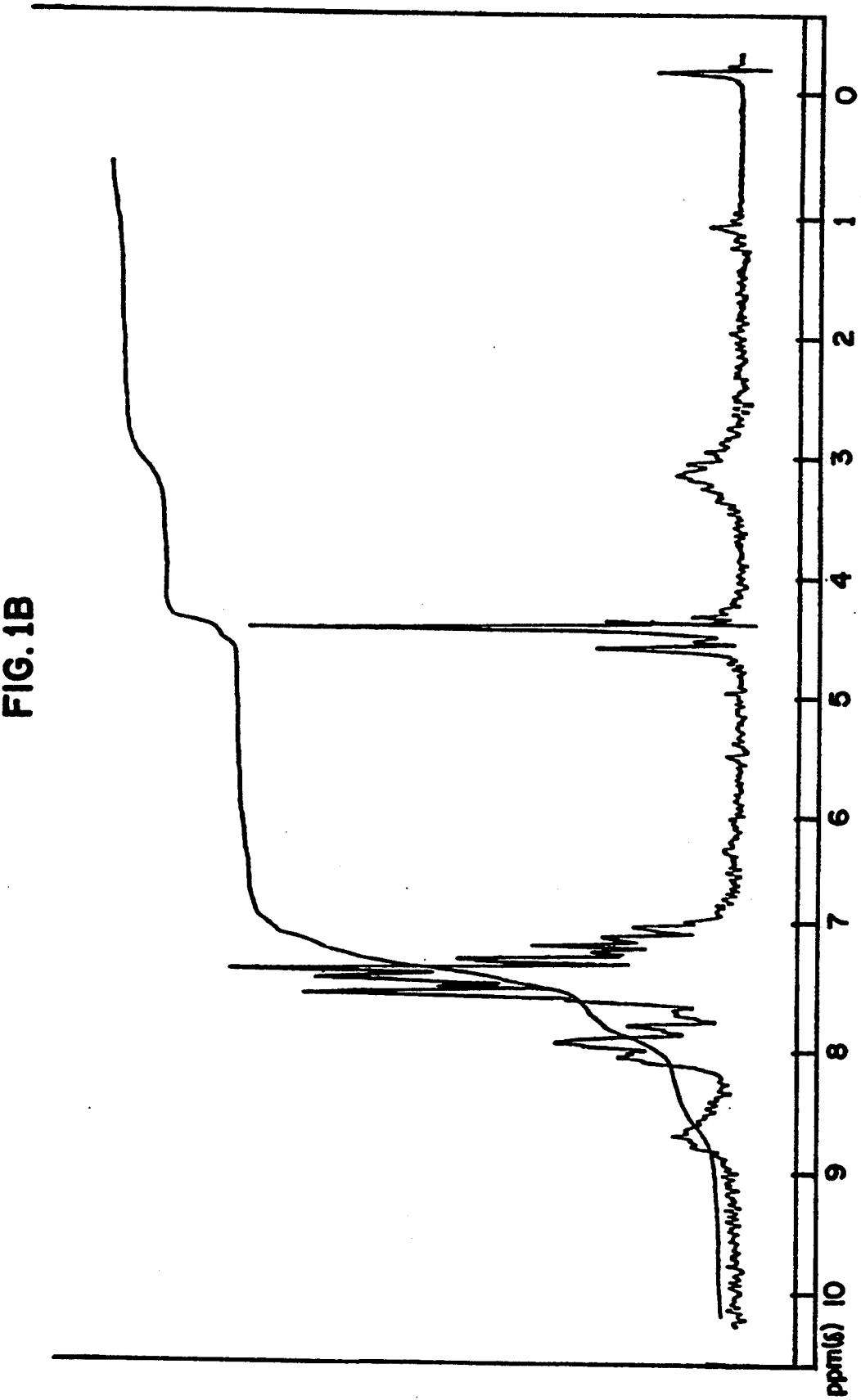

The above sequence reaction was repeated with shorter time of quenching with a solution of in water Na$_2$CO$_3$, e.g., 10 minutes followed by extraction. NMR still the same. (FIG. 1B).

EXAMPLE 8

(1) N-methyl-4-[2-(4-hydroxymethylphenyl)ethenyl) quinolinium methosulfate
(2) N-methyl-4-[2-(4-chloromethylphenyl)ethenyl] quinolinium methosulfate and chloride mixed salt 3.6 g of (1) was added dropwise to 3 mL of SOCl$_2$ (freshly distilled) and stirring was initiated and continued for 30 minutes. To a resulting solution, 30 mL of Et₂O was added slowly (over about 1 hour), and the resulting orange crystals were collected by filtration. The yield of crystals was 3.0 g. NMR data indicates that the desired product (2) was obtained.

EXAMPLE 9

(1) 4-[2-(4-hydroxymethylphenyl)ethenyl]quinoline
(2) 4-[2-(4-chloromethylphenyl)ethenyl]quinolinium hydrochloride 1 mM of (1) was added to an excess of SOCl₂ and stirred for three hours. Product was precipitated with Et₂O, filtered and dried in vacuo. Yield of the yellow crystals was 0.242 g (86%) mp=260° C. (decomposed). Elemental analysis (Theoretical: C=68.37, H=4.78. N=4.43 and Cl=22.42. Actual: C=67.21, H=4.69, N=4.33, and Cl=22.00) and NMR(CDCl₃/CD₃OD; 200 MHz) confirmed structure. The resulting product (2) was exposed to light (OLITE AL 53/100, 5 kw, L1261 lamp at 40 in).

UV spectral data indicated that the photoactivity remained after quaternization.

EXAMPLE 10

Synthesis of photopolymer (1) 4-[2-(4-chloromethylphenyl)ethenyl]quinolinium hydrochloride (2.61 g)
(2) N-methyl-4-[2-(4-chloromethylphenyl)ethenyl] quinolinium methosulfate and chloride mixed salt (2.81 g)
(3) poly(4-vinylpyridine) (50,000 mw), 16–22% in MeOH
(4) poly(4-vinylpyridine) (200,000 mw), 20⅜26% in MeOH (1) as prepared in Example 9 and (2) prepared in Example 8 were combined and reacted with (3) and (4) as illustrated in Table II below.

The mixtures were stirred until completely dissolved, and stirring was continued overnight at room temperature.

TABLE II

| | (I) | (II) |
|---|---|---|
| (3) | 28 g of (3) (16–22% PVPy solution in MeOH) + 1.4 g of (1) (≈8%) (A) | 28 g of (3) (16–22% PVPy solution in MeOH) + 1.2 g of (2) (C) |
| (4) | 23 g of (4) (20–26% PVPy in MeOH) + 1.4 g of (1) (≈8%) (B) | 23 g of (4) (20–26% PVPy solution in MeOH) + 1.2 g of (2) (D) |

After stirring overnight solution D turned to gel. A, B, C, were used to make a screen printing plate. After irradiation (LITE AL 53/100, 5kw, L1261 lamp at 40 in) and washing with high pressure water, A washed out and B and C exhibited very weak image. All solutions (A, B, C) were heated overnight at +45 (±5° C.) and checked again. All of them gave an image.

Figure 2A:
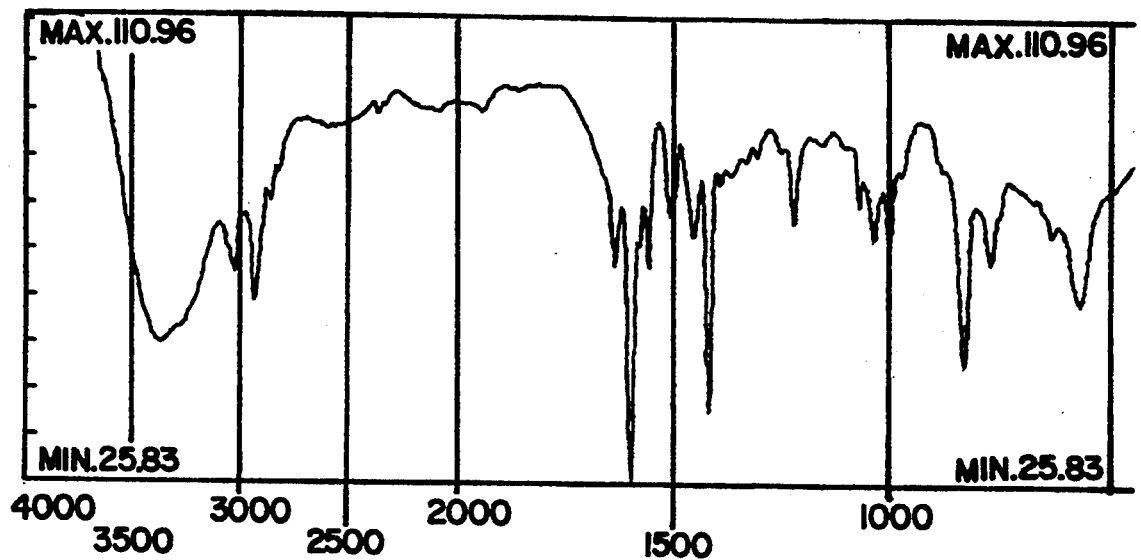
FIGS. 2A, 2B, and 2C represent graphs of the result of IR spectroscopy of photopolymers of our invention.
Figure 2B:
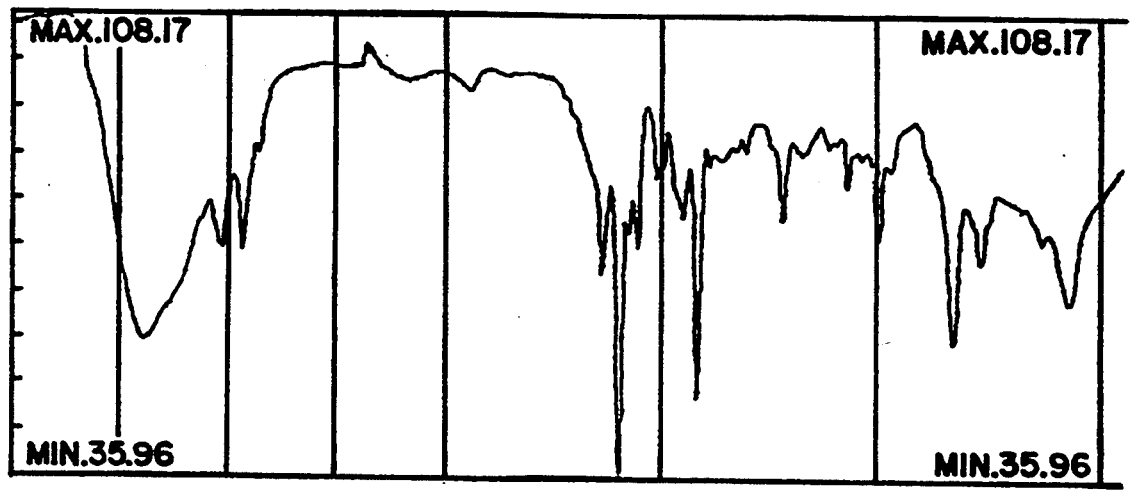
Figure 2C:
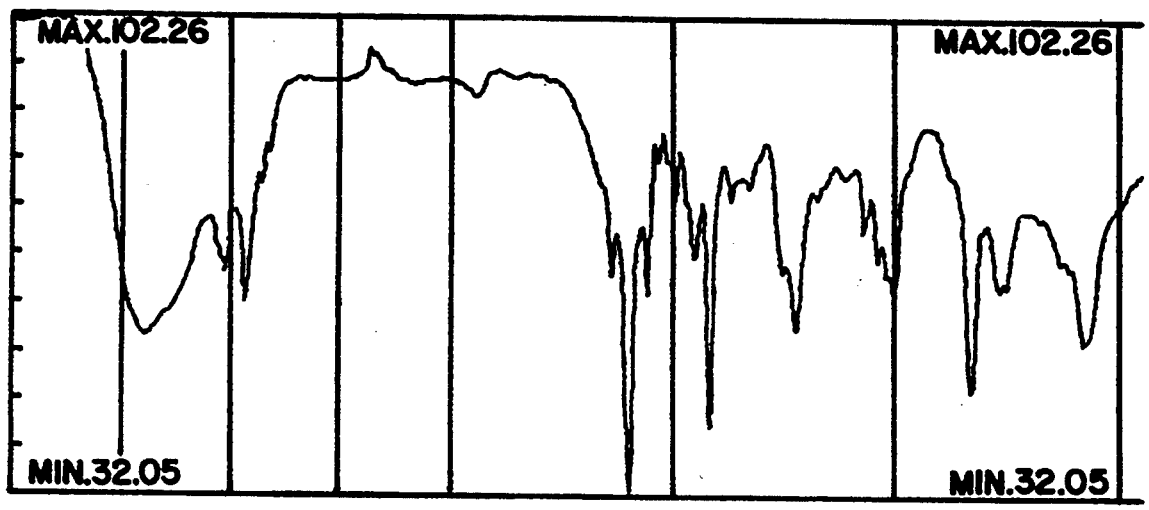

The resulting IR spectroscopic data confirmed that reactants (1) and 2) were grafted onto the poly(vinyl-pyridine). (FIG. 2A, 2B, 2C).

The foregoing description, examples and data are illustrative of the invention described herein, and they should not be used to unduly limit the scope of the invention or the claims. Since many embodiments and variations can be made while remaining within the spirit and scope of the invention, the invention resides wholly in the claims herein after appended.

What is claimed is:

1. A photosensitive polymer composition comprising pH sensitive units having the general structure:

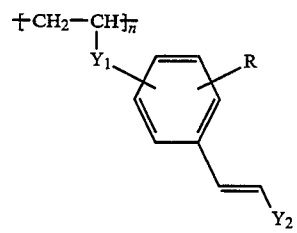

wherein R is hydrogen alkyl, alkoxy, aldehyde, carboxyl, oxy, hydroxyl, aryl, aryloxy, halo, cyanop, or amino; $Y_1$ comprises, a quaternary heterocyclic nitrogen-containing organic moiety having about 1 to 26 carbon atoms linked through the atoms of the heterocycle, or a quaternary heterocyclic nitrogen-containing organic moiety having about 1 to 26 carbon atoms linked through at least one $C_{1-6}$ alkyl substituent; $Y_2$ comprises a quaternary heterocyclic nitrogen-containing organic moiety having about 1 to 26 carbon atoms; and the photosensitive polymer has a molecular weight of about 1,000 to 1,000,000.

2. The composition of claim 1 wherein $Y_1$ is a derivative of benzothiazole, morpholine, oxazole, isoxazole, piperazine, piperidine, purine, pyrazine, pyrimidine, quinazoline, quinoline, quinoxazoline, or tetrazole.

3. The composition of claim 2 wherein $Y_1$ is linked to the benzyl ring through a quaternary nitrogen atom.

4. The composition of claim 1 wherein $Y_1$ is pyridine.

5. The composition of claim 1 wherein $Y_2$ is a derivative of benzothiazole, morpholine, oxazole, isoxazole, piperazine, piperidine, purine, pyrazine, pyridine, pyrimidien, quinazoline, quinoline, quinoxazoline, or tetrazole.

6. The composition of claim 1 wherein $Y_2$ is a quaternary, heterocyclic nitrogen-containing organic moiety having the formula:

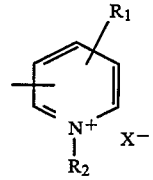

wherein $R_1$ is hydrogen, alkyl, alkoxy, aldehyde, carboxyl, oxy, hydroxyl, aryl, aryloxy, halo, cyano, or amino; $R_2$ is a H or a $C_{1-12}$ branched or unbranched alkyl group; and $X^-$ is an anion selected from the group consisting of halide, alkyl sulfate, alkyl sulfonate, alkyl phosphate, alkyl hexaphosphate, alkyl phosphonate, or boron tetrafluoride.

7. The composition of claim 1 wherein $Y_2$ is a quaternary, heterocyclic nitrogen-containing organic moiety having the formula:

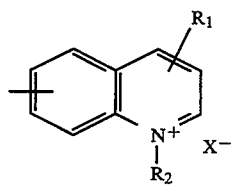

wherein $R_1$ is hydrogen, alkyl, alkoxy, aldehyde, carboxyl, oxy, hydroxyl, aryl, aryloxy, halo, cyano, or amino; $R_2$ is hydrogen or a $C_{1-12}$ branched or unbranched alkyl group; and $X^-$ is an anion selected from the group consisting of halide, alkyl sulfate, alkyl sulfonate, alkyl phosphate, alkyl hexaphosphate, alkyl phosphonate, or boron tetrafluoride.

8. A photosensitive polymer comprising:

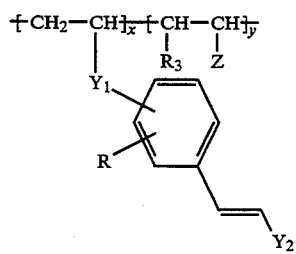

wherein x is about 0.05 to 20 mole-%; y is about 99.95 to 80 mole-%; each R and $R_3$ are independently hydrogen, $C_{1-6}$ branched or unbranched alkyl, alkoxy, aldehyde, carboxyl, oxy, hydroxyl, aryl, aryloxy, halo, cyano, or amino; $Y_1$ is a quaternary heterocyclic nitrogen-containing organic moiety having about 1 to 26 carbon atoms linked through the atoms of the heterocycle, or a quaternary heterocyclic nitrogen-containing organic moiety having about 1 to 26 carbon atoms linked through at least one $C_{1-6}$ alkyl substituent; $Y_2$ is a quaternary heterocyclic nitrogen-containing organic moiety having about 1 to 26 carbon atoms; Z is hydrogen, alkyl, ester, alkoxy, aldehyde, carboxyl, oxy, hydroxyl, aryl, aryloxy, halo, cyano, amino, or a heterocyclic nitrogen-containing organic moiety having about 1 to 26 carbon atoms; and the photosensitive polymer has a molecular weight of about 1,000 to 1,000,000.

9. The composition of claim 8 wherein $Y_1$ is a derivative of benzothiazole, morpholine, oxazole, isoxazole, piperazine, piperidine, purine, pyrazine, pyridine, pyrimidine, quinazoline, quinoline, quinoxazoline, or tetrazole.

10. The composition of claim 9 wherein $Y_1$ is a derivative of pyridine.

11. The composition of claim 9 wherein $Y_1$ is linked to the benzyl ring through the quaternary nitrogen atom.

12. The composition of claim 8 wherein $Y_2$ is a derivative of benzothiazole, morpholine, oxazole, isoxazole, piperazine, piperidine, purine, pyrazine, pyridine, pyrimidine, quinazoline, quinoline, quinoxazoline, or tetrazole.

13. The composition of claim 8 wherein $Y_2$ is a quaternary, heterocyclic nitrogen-containing moiety having the formula:

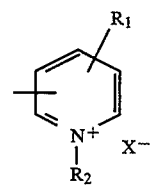

wherein $R_1$ is hydrogen, alkyl, alkoxy, aldehyde, carboxyl, oxy, hydroxyl, aryl, aryloxy, halo, cyano, or amino; $R_2$ is hydrogen or a $C_{1-12}$ branched or unbranched alkyl group; and $X^-$ is an anion selected from the group consisting of halide, alkyl sulfate, alkyl sulfonate, alkyl phosphate, alkyl hexaphosphate, alkyl phosphonate, or boron tetrafluoride.

14. The composition of claim 8 wherein $Y_2$ comprises a quaternary, heterocyclic nitrogen-containing moiety having the formula:

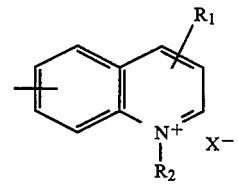

wherein $R_1$ is hydrogen, alkyl, alkoxy, aldehyde, carboxyl, oxy, hydroxyl, aryl, aryloxy, halo, cyano, or amino; $R_2$ is hydrogen or a $C_{1-12}$ branched or unbranched alkyl group; and $X^-$ is an anion selected from the group consisting of halide, alkyl sulfate, alkyl sulfonate, alkyl phosphate, alkyl hexaphosphate, alkyl phosphonate, or boron tetrafluoride.

15. A photosensitive polymer comprising:

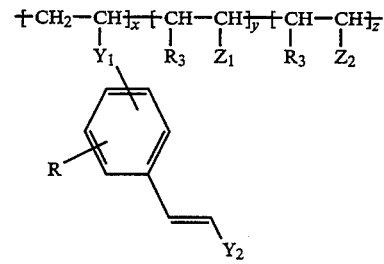

wherein x is about to 0.05 to 20 mole-%; y is about 0 to 99.95 mole-%; z is about 0 to 99.95 mole-%; each R and $R_3$ are independently hydrogen, $C_{1-6}$ branched or unbranched alkyl, alkoxy, aldehyde, carboxyl, oxy, hydroxyl, aryl, aryloxy, halo, cyano, or amino; $Y_1$ is a quaternary heterocyclic nitrogen-containing organic moiety having about 1 to 26 carbon atoms linked through the atoms of the heterocycle, or a quaternary heterocyclic nitrogen-containing organic moiety having about 1 to 26 carbon atoms linked through at least one $C_{1-6}$ alkyl substituent; $Y_2$ is a quaternary heterocyclic nitrogen-containing organic moiety having about 1 to 26 carbon atoms; $Z_1$ and $Z_2$ are independently hydrogen, alkyl, ester, alkoxy, aldehyde, carboxyl, oxy, aryl, aryloxy, halo, cyano, amino, or a heterocyclic nitrogen-containing organic moiety having about 1 to 26 carbon atoms; and the photosensitive polymer has a molecular weight of about 1,000 to 1,000,000.

16. The composition of claim 15 wherein $Y_1$ is a derivative of benzothiazole, morpholine, oxazole, isoxazole, piperazine, piperidine, purine, pyrazine, pyridine, pyrimidine, quinazoline, quinoline, quinoxazoline, or tetrazole.

17. The composition of claim 16 wherein $Y_1$ is a derivative of pyridine.

18. The composition of claim 17 wherein $Y_1$ is linked to the benzyl ring through a quaternary nitrogen atom of the pyridine ring.

19. The composition of claim 15 wherein $Y_2$ is a derivative of benzothiazole, morpholine, oxazole, isoxazole, piperazine, piperidine, purine, pyrazine, pyridine, pyrimidine, quinazoline, quinoline, quinoxazoline, or tetrazole.

20. The composition of claim 15 wherein $Y_2$ is a quaternary, heterocyclic nitrogen-containing moiety having the formula:

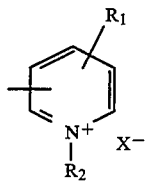

wherein $R_1$ is hydrogen, alkyl, alkoxy, aldehyde, carboxyl, oxy, hydroxyl, aryl, aryloxy, halo, cyano, or amino; $R_2$ is hydrogen or a $C_{1-12}$ branched or unbranched alkyl group; and $X^-$ is an anion selected from the group consisting of halide, alkyl sulfate, alkyl sulfonate, alkyl phosphate, alkyl hexaphosphate, alkyl phosphonate, or boron tetrafluoride.

21. The composition of claim 15 wherein $Y_2$ is a quaternary, heterocyclic nitrogen-containing moiety having the formula:

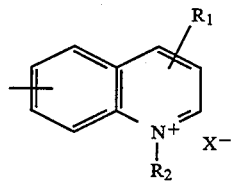

wherein $R_1$ is hydrogen, alkyl, alkoxy, aldehyde, carboxyl, oxy, hydroxyl, aryl, aryloxy, halo, cyano, or amino; $R_2$ is hydrogen or a $C_{1-12}$ branched or unbranched alkyl group; and $X^-$ is an anion selected from the group consisting of halide, alkyl sulfate, alkyl sulfonate, alkyl phosphate, alkyl hexaphosphate, alkyl phosphonate, or boron tetrafluoride.

22. A photosensitive polymer comprising a polymer comprising repeating units of the formula:

wherein each R and $R_3$ are independently hydrogen, $C_{1-6}$ branched or unbranched alkyl, alkoxy, aldehyde, carboxyl, oxy, hydroxyl, aryl, aryloxy, halo, cyano, or amino; $R_2$ is hydrogen or a $C_{1-12}$ branched or unbranched alkyl group; x is about 0.5 to 20 mole-%; y is about 99.5 to 80 mole-%; m and n are independently about 0 to 6; $X^-$ is an anion selected from the group consisting of halide, alkyl sulfate, alkyl sulfonate, alkyl phosphate, alkyl hexaphosphate, alkyl phosphonate, or boron tetrafluoride; Z is $C_{1-4}$ alkyl, carboxylic, aryl, benzyl, halo, an amine moiety, or a heterocyclic nitrogen-containing organic moiety having about 1 to 26 carbon atoms; and the photosensitive polymer has a molecular weight of about 1,000 to 1,000,000.

23. The photosensitive polymer composition of claim 22 wherein m is about 1 to 6.

24. A liquid photoresist composition comprising:
 (a) an effective amount of a liquid carrier; and
 (b) about 1 to 99 wt-% of a photosensitive polymer having pH sensitive units and units of the formula:

wherein R is hydrogen, alkyl, alkoxy, aldehyde, carboxyl, oxy, hydroxyl, aryl, aryloxy, halo, cyano, or amino; $Y_1$ is a quaternary heterocyclic nitrogen-containing organic moiety having about 1 to 26 carbon atoms linked through the atoms of the heterocycle, or quaternary heterocyclic nitrogen-containing organic moiety having about 1 to 26 carbon atoms linked through at least one $C_{1-6}$ alkyl substituent; and $Y_2$ is a quaternary heterocyclic nitrogen-containing organic moiety having about 1 to 26 carbon atoms.

25. The composition of claim 24 wherein the liquid carrier comprises an organic solvent.

26. The composition of claim 24 wherein the composition is an aqueous emulsion.

27. The composition of claim 24 wherein the liquid carrier comprises water.

28. A photoresist film comprising:

(a) a photosensitive polymer having pH sensitive units and units of the formula:

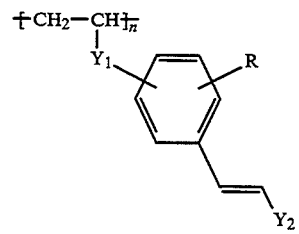

wherein R is hydrogen, alkyl, alkoxy, aldehyde, carboxyl, oxy, hydroxyl, aryl, aryloxy, halo, cyano, or amino; $Y_1$ comprises a quaternary heterocyclic nitrogen-containing organic moiety having about 1 to 26 carbon atoms linked through the atoms of the heterocycle, or a quaternary heterocyclic nitrogen-containing organic moiety having about 1 to 26 carbon atoms linked through at least one $C_{1-6}$ alkyl substituent; and $Y_2$ comprises a quaternary heterocyclic nitrogen-containing organic moiety having about 1 to 26 carbon atoms.

29. A screen printing stencil comprising the photoresist film of claim 28.

30. A flexible lithographic plate comprising the photoresist film of claim 28.

* * * * *

UNITED STATES PATENT AND TRADEMARK OFFICE
CERTIFICATE OF CORRECTION

PATENT NO. : 5,334,485

DATED : August 2, 1994

INVENTOR(S) : Van Iseghem et al.

It is certified that error appears in the above-identified patent and that said Letters Patent is hereby corrected as shown below:

On column 3, line 32, please delete "waterresistant" and substitute therefore --water-resistant--

On column 5, lines 22 and 48, please delete "aidehyde" and substitute therefore --aldehyde--

On column 6, lines 23 and 57, please delete "aidehyde" and substitute therefore --aldehyde--

On column 8, line 56, please delete "aidehyde" and substitute therefore --aldehyde--

On column 9, line 56, please delete "aidehyde" and substitute therefore --aldehyde--

On column 10, line 30, please delete "aidehyde" and substitute therefore --aldehyde--

On column 10, line 62, please delete "aidehyde" and substitute therefore --aldehyde--

On column 5, line 55, please insert $--C_{1-6}--$ after the word "one"

On column 7, line 61, please delete "$I^{31}$" and substitute therefore $--I^---$

UNITED STATES PATENT AND TRADEMARK OFFICE
CERTIFICATE OF CORRECTION

PATENT NO. : 5,334,485
DATED : August 2, 1994
INVENTOR(S) : Van Iseghem et al.

It is certified that error appears in the above-identified patent and that said Letters Patent is hereby corrected as shown below:

On column 9, line 13, please delete "photocrosslinkability" and substitute therefore --photocross-linkability--

On column 9, line 27, please delete "iraconic" and substitute therefore --itaconic--

On column 14, line 46, please delete "desireable" and substitute therefore --desirable--

On column 14, line 61, please delete "4,567,580" and substitute therefore --4,564,580--

On column 15, line 20, please delete "photo cross" and substitute therefore --photocross--

On column 19, line 19, please delete "MH$_z$)" and substitute therefore --MHz)--

On column 19, line 34, please delete "20 3/8" and substitute therefore --20- --

On column 19, line 56, please delete "(LITE" and substitute therefore --(OLITE--

On column 20, line 4 (claim 1), please delete "composition" after the word "polymer"

On column 20, line 19, please delete "cyanop" and substitute therefore --cyano--

UNITED STATES PATENT AND TRADEMARK OFFICE
CERTIFICATE OF CORRECTION

PATENT NO. : 5,334,485

DATED : August 2, 1994

INVENTOR(S) : Van Iseghem et al.

It is certified that error appears in the above-identified patent and that said Letters Patent is hereby corrected as shown below:

On column 20, lines 20 and 27, please delete "comprises" and substitute therefore --is--

On column 20, line 43 (claim 5), please delete "pyrimidien" and substitute therefore --pyrimidine--

On column 22, line 17 (claim 14), please delete "comprises" and substitute therefore --is--

On column 26, lines 14 and 20 (claim 28), please delete "comprises" and substitute therefore --is--

Signed and Sealed this

Thirteenth Day of December, 1994

Attest:

BRUCE LEHMAN

*Attesting Officer*     *Commissioner of Patents and Trademarks*